(12) United States Patent
Sauer

(10) Patent No.: US 12,157,262 B2
(45) Date of Patent: Dec. 3, 2024

(54) MACHINE SYSTEM FOR PRODUCING OR TREATING SYNTHETIC THREADS

(71) Applicant: Oerlikon Textile GmbH & Co. KG, Remscheid (DE)

(72) Inventor: Arnulf Sauer, Lennestadt (DE)

(73) Assignee: Oerlikon Textile GmbH & Co. KG, Remscheid (DE)

( * ) Notice: Subject to any disclaimer, the term of this patent is extended or adjusted under 35 U.S.C. 154(b) by 1091 days.

(21) Appl. No.: 16/761,936

(22) PCT Filed: Nov. 6, 2018

(86) PCT No.: PCT/EP2018/080274
§ 371 (c)(1),
(2) Date: May 6, 2020

(87) PCT Pub. No.: WO2019/091955
PCT Pub. Date: May 16, 2019

(65) Prior Publication Data
US 2020/0324454 A1    Oct. 15, 2020

(30) Foreign Application Priority Data

Nov. 10, 2017  (DE) .................... 10 2017 010 473.5

(51) Int. Cl.
| | | |
|---|---|---|
| *B29C 48/92* | (2019.01) | |
| *B29C 48/05* | (2019.01) | |
| *D01D 5/08* | (2006.01) | |
| *D01D 13/02* | (2006.01) | |
| *G01N 33/36* | (2006.01) | |

(52) U.S. Cl.
CPC ............. *B29C 48/92* (2019.02); *B29C 48/05* (2019.02); *D01D 5/08* (2013.01); *D01D 13/02* (2013.01); *G01N 33/365* (2013.01); *B29C 2948/92019* (2019.02); *B29C 2948/92209* (2019.02); *B29C 2948/9238* (2019.02)

(58) Field of Classification Search
CPC ................... B29C 48/92; B29C 48/05; B29C 2948/92209; B29C 2948/9238; B29C 2948/92019; D01D 5/08; D01D 13/02; G01N 33/365
See application file for complete search history.

(56) References Cited

FOREIGN PATENT DOCUMENTS

| | | |
|---|---|---|
| CN | 1616723 A | 5/2005 |
| CN | 1960309 A | 5/2007 |
| CN | 111344447 B | 6/2022 |
| DE | 10039093 A1 | 3/2001 |

(Continued)

OTHER PUBLICATIONS

Machine Translation of WO 2011069911 A1, PE2E Search, p. 1-8. (Year: 2011).*

*Primary Examiner* — Robert J Eom
(74) *Attorney, Agent, or Firm* — BainwoodHuang

(57) ABSTRACT

Techniques involve a machine system for producing or treating synthetic threads, comprising a plurality of machine components, having actuators and/or sensors, that are associated with a plurality of control components. The control components are connected by a machine network to a central machine control station. In order to remedy process disruptions as quickly as possible and to ensure uniform product quality, the control components are coupled in parallel to a central analysis station by an analysis network.

8 Claims, 4 Drawing Sheets

(56) References Cited

FOREIGN PATENT DOCUMENTS

Figure 1:
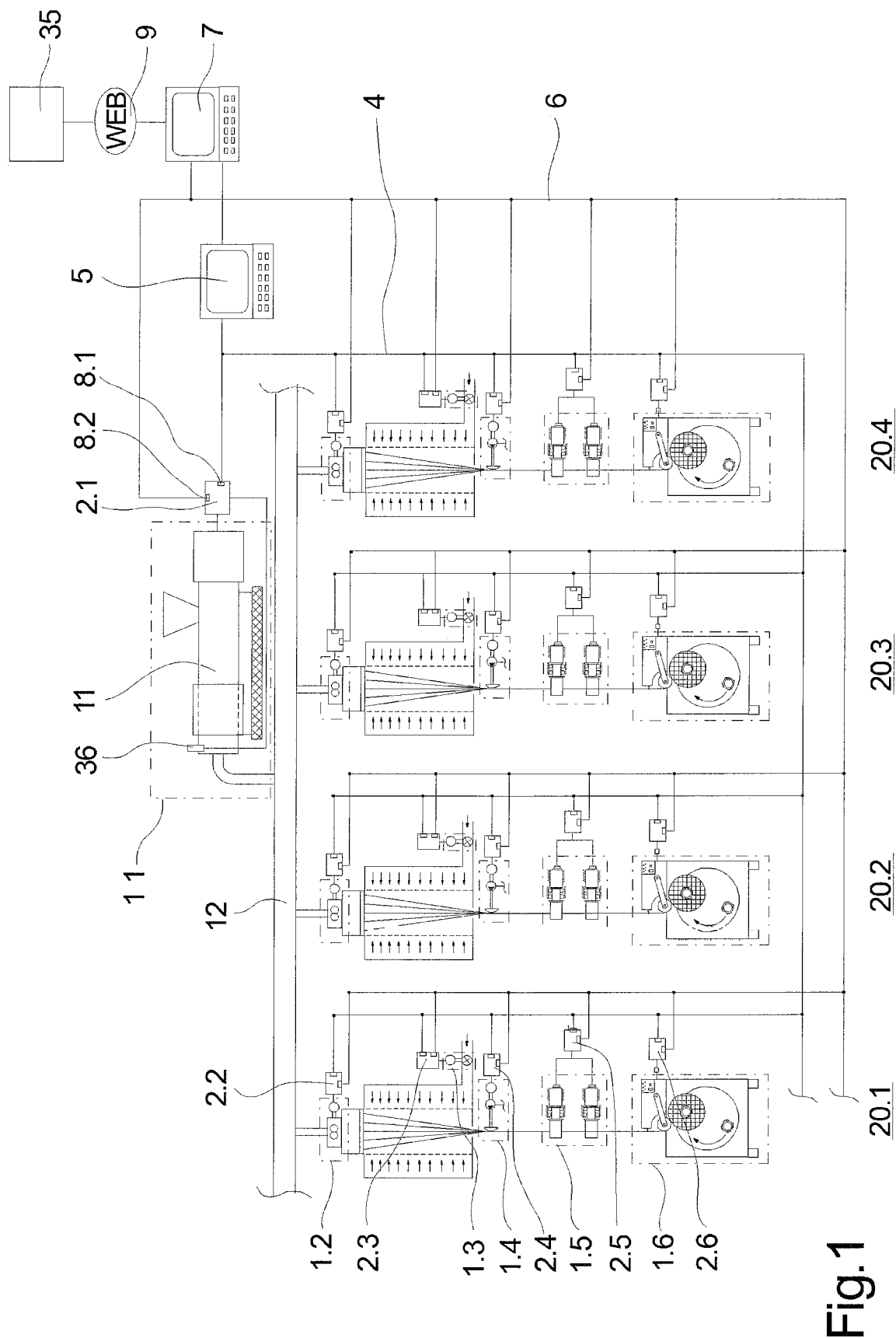

| | | |
|---|---|---|
| DE | 10250442 A1 | 5/2003 |
| DE | 10254010 A1 | 6/2004 |
| DE | 102015002922 A1 | 9/2016 |
| WO | WO-2011069911 A1 * | 6/2011 ............. B29C 48/92 |

* cited by examiner

MACHINE SYSTEM FOR PRODUCING OR TREATING SYNTHETIC THREADS

The present invention relates to a machine system for producing or treating synthetic yarns as disclosed herein.

When producing synthetic yarns, for example, during melt spinning or during the treatment of synthetic yarns, for example, during false twist texturing, a plurality of individual production processes, such as extrusion, texturing, drawing, intermingling, and spooling, influence the quality of the yarns. For its part, each individual production process can be influenced by a plurality of parameters. To this extent, a plurality of machine components are used which have actuators and sensors in order to influence the production process and the yarn quality in the desired manner Each of the machine components is associated with a control component which is connected to a central machine control station via a machine network. Such a machine system for producing or treating synthetic yarns is, for example, known from DE 10 2015 002 922 A1.

In the known machine system, all data and signals exchanged for controlling the production processes are transmitted via a machine network. The machine network generally comprises a bus system via which the parameters needed for control are transmitted. In particular in the case of unallowable deviations in the process and in the product, rapid reaction times are desirable so that the corresponding machine components can be controlled. However, the transmission speed and the transmission capacity of such bus systems is limited.

The object of the present invention is to improve the generic machine system for producing or treating synthetic yarns in such a way that a most consistent possible process quality is ensured when producing or treating the synthetic yarns.

A further object of the present invention is to further develop the generic machine system in such a way that fastest-possible analyses and rapid reaction times are achievable in the case of process disturbances.

This object is achieved according to the present invention in that the control components are coupled in parallel to a central analysis station via an analysis network.

Advantageous refinements of the present invention are defined via the features and feature combinations disclosed herein.

The present invention has the particular advantage that the data transfer required for controlling the machine components and the data transfer required for analyzing the process are separated. Thus, the data and parameters exchanged for the analysis for determining process disturbances can be directly transmitted via a separate analysis network which couples the control components directly to a central analysis station. The data required for controlling the machine components are conveyed to the control components via the machine network as usual. Thus, existing software structures can be used both for analysis and for control.

Here, in particular the refinement of the present invention, in which the analysis network is formed by a real time-capable bus system for data transmission, has proven to be of value. Thus, data transmission in real time is possible. By means of minimal time intervals between a data occurrence and a data analysis, processes disturbances can be rapidly analyzed and corrected both during the production of synthetic yarns and during the treatment of synthetic yarns. Thus, pure real-time data analyses can be carried out inside the analysis station, which in particular foster a rapid diagnosis in the case of process disturbances.

The machine network is configured for data transmission preferably via an Industrial Ethernet. Thus, the required parameters for controlling the machine components can be transmitted independently of the real time-capable analysis network, for example, a ProfiNet.

In order to enable a parallel data transfer via the machine network and via the analysis network, the refinement of the present invention, in which the control components have at least two network connections, is particularly advantageous, wherein one of the network connections is implemented as a real-time network connection. In this respect, it is already possible to carry out a preselection or preprocessing of the parameters inside the control components, it then being possible to convey said parameters directly to the analysis station via the real-time network connection and the real-time analysis network.

Generally, it is possible to route individual real-time parameters, for example, a yarn tension measured value, directly to the machine control station, in order to enable direct control interventions, taking into consideration an actual-setpoint comparison. For this purpose, the refinement of the present invention is provided in which the machine control station is connected to the analysis network via a separate real-time network connection.

With regard to complex data structures and a plurality of parameters, it is also advantageously possible to connect the analysis station to an external diagnosis station. For this purpose, the analysis station advantageously has an Internet interface in order, for example, to enable big data analysis.

Thus, it is particularly advantageous if the analysis station and the machine control station are interconnected for data exchange. Rapid reaction times for maintaining certain product qualities or for eliminating process disturbances may thereby be ensured.

Due to the highly complex structure and the plurality of machine components, it is furthermore provided that the machine network and/or the analysis network are configured wirelessly according to a WLAN standard. The machine network may thereby advantageously be configured as a radio network.

The present invention will be described in greater detail with reference to the attacked figures.

Figure 2:
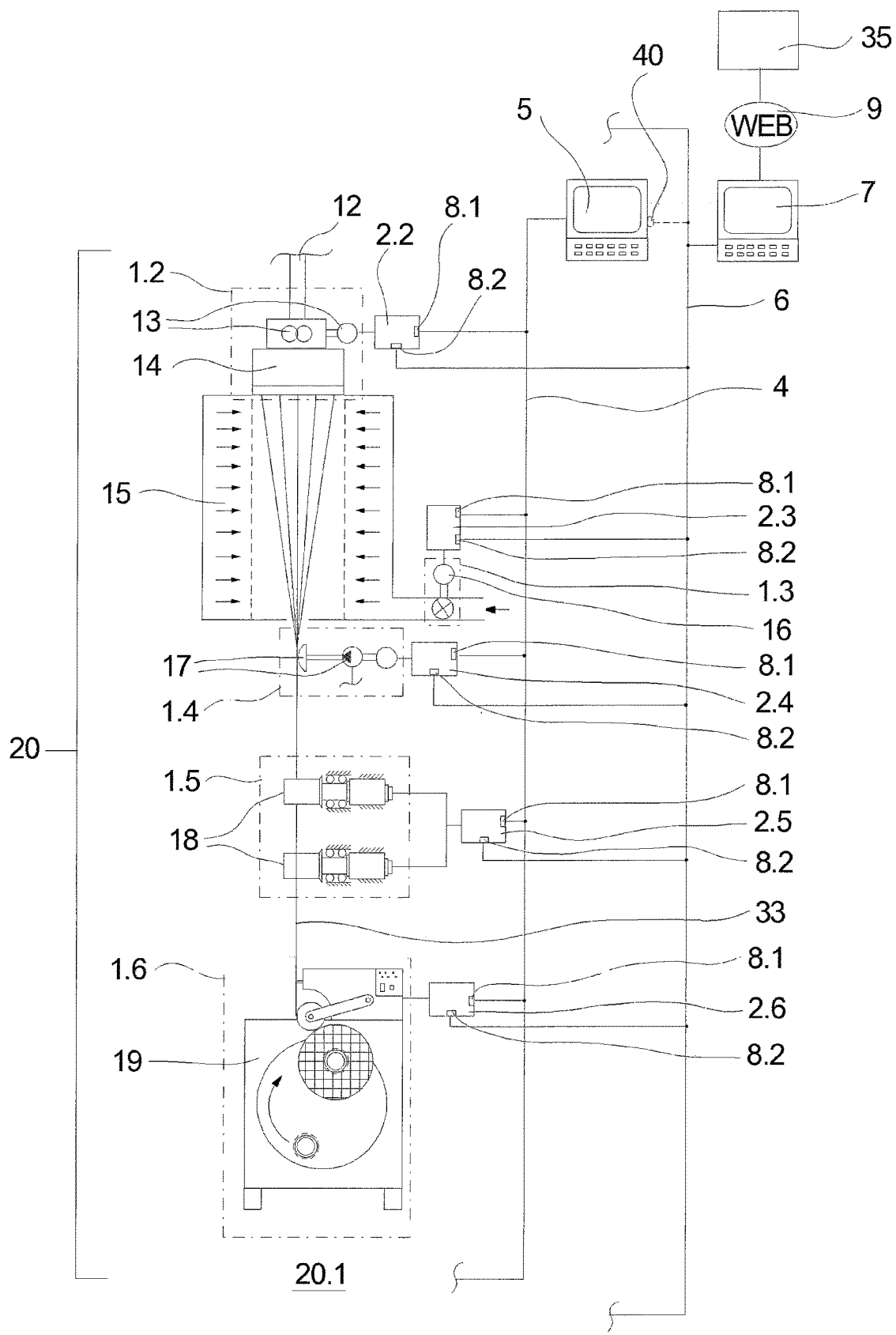
Figure 3:
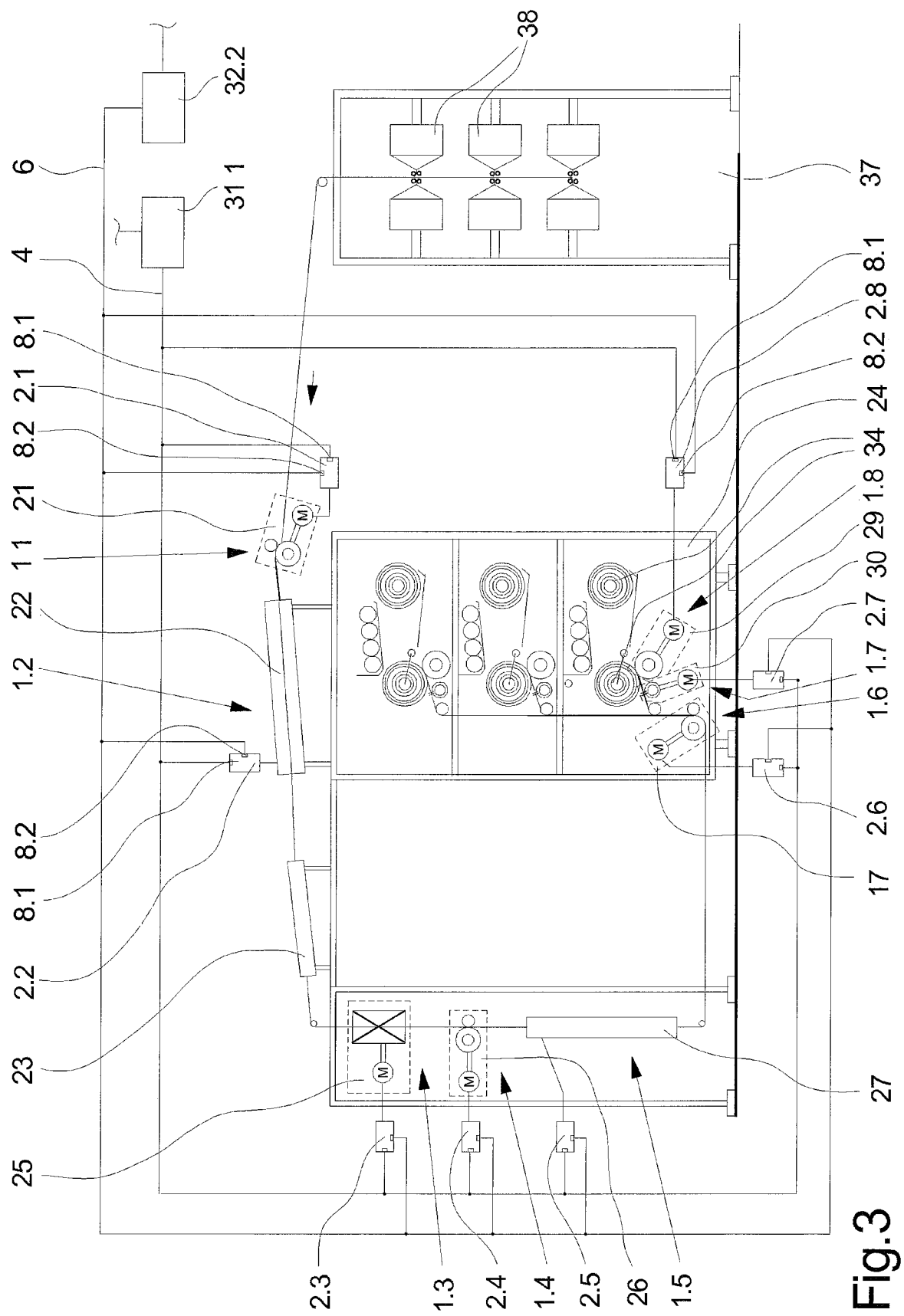
Figure 4:
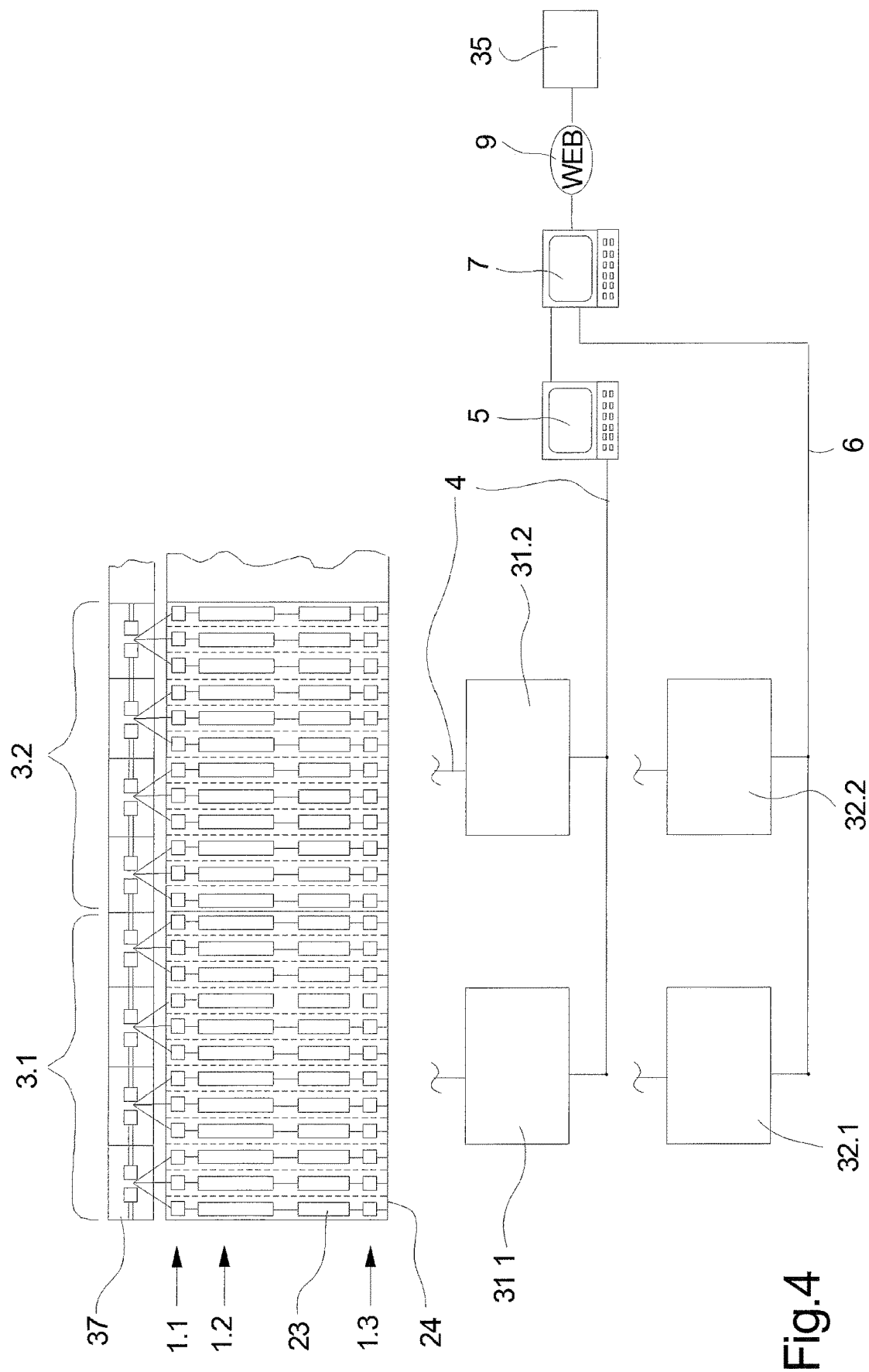

The following are depicted:

FIG. 1 schematically depicts a first exemplary embodiment of a machine system for producing synthetic yarns;

FIG. 2 schematically depicts one of the machine sections of the exemplary embodiment from FIG. 1;

FIG. 3 schematically depicts a cross-sectional view of a further exemplary embodiment of a machine system for texturing synthetic yarns;

FIG. 4 schematically depicts a top view of an exemplary embodiment from FIG. 3.

FIGS. 1 and 2 depict a first exemplary embodiment of a machine system according to the present invention for producing synthetic yarns, in several views. FIG. 1 schematically depicts an overall view of the machine system, and FIG. 2 schematically depicts a partial view of the machine system. If no explicit reference is made to one of the figures, the following description applies to both figures.

The machine system has a plurality of machine components in order to control the production process for the melt spinning of synthetic yarns. A first machine component 1.1 is formed by an extruder 11 which is connected to a plurality of spinning positions 20 via a melt line system 12. FIG. 1 depicts four spinning positions 20.1 to 20.4.

The spinning positions 20 are configured identically and are schematically depicted in FIG. 2. Inside the spinning position 20, several machine components 1.2, 1.3, 1.4, 1.5, and 1.6 are provided, in order to control the spinning of a yarn sheet within the spinning positions 20. In this respect, a yarn sheet of, for example, 12, 16, or 32 yarns is produced in each spinning position depicted in FIG. 1. The yarn sheet is indicated by the reference number 33 in FIG. 2.

In this exemplary embodiment, the term "machine components" refers to the machine parts which are significantly involved in the process via drives, actuators, and sensors. In addition to the drives and actuators, sensors, which are not depicted in greater detail here, are also associated with the machine components, which are necessary for controlling the production process. Thus, the spinning position 20 has, as a first component 1.2, a spinning pump apparatus 13 which is connected to a melt line system 12 and which interacts with a spinneret 14 for extruding the yarns. Typically, a pressure sensor and possibly a temperature sensor are associated with the spinning pump apparatus 13. A second machine component 1.3 is formed by a blower unit 16, which controls a cool-air supply of a cooling apparatus 15. The cooling apparatus 15 is arranged below the spinneret 14.

A next process step is carried out by the machine component 1.4, which comprises a wetting apparatus 17. The guiding of the yarn sheet 33 for drawing off and drawing the yarns is carried out by a machine component 1.5, which has a godet unit 18. At the end of the production process, the yarns are wound into spools; for this purpose, the machine component 1.6 is provided, which forms the spooling machine 19.

Inside the spinning positions 20.1 to 20.4, one of several control components 2.2 to 2.6 is associated with the machine components 1.2 to 1.6 in each case. The machine component 1.2 and the control component 2.2 thus form a unit. Accordingly, the machine components 1.3 to 1.6 are connected to the associated control components 2.3 to 2.6.

For communication and data transmission, each of the control components 2.2 to 2.6 respectively has two network connections 8.1 and 8.2. The network connection 8.2 has real-time capability, in order to enable real-time data transmission. Thus, the real-time network connections 8.2 of the control components 2.2 to 2.6 are coupled to one another to a real time-capable analysis network 6, for example, a ProfiNet or another real-time bus system. The analysis network 6 is connected to an analysis station 7 in order to route the data transmitted by the control components 2.2 to 2.6 directly to the analysis station 7.

For communication and for data transmission, the control components 2.2 to 2.6 are connected to a machine network 4 via the network connections 8.1. The machine network 4, which is preferably formed by an Industrial Ethernet, connects the control components 2.2 to 2.6 to a central machine control station 5. By means of the isolated networks 4 and 6, it is possible to carry out the communication and data transmission for the control of the machine components in parallel with communication and data transmission with the analysis station. Thus, in particular real-time parameters can be included for analysis, so that the process disturbances are quickly remedied and so that uniform product qualities are ensured.

In order to improve the control of the machine components, in an alternative embodiment variant, the machine control station 5 has a real time-capable network connection 40, by means of which a direct connection to the analysis network is possible. Thus, it is possible, for example, to transmit certain real-time parameters such as a yarn tension measured value directly to the machine control station 5 and to use at least one of the machine components for control. In FIG. 2, this embodiment having the real-time network connection 40 is depicted by a dashed line.

As depicted in FIG. 1, the machine system comprises several spinning positions, wherein here, only four of the spinning positions are depicted. The spinning positions 20.2, 20.3, and 20.4 which are adjacent to the spinning position 20.1 are identically configured and have a plurality of machine components in each case. The spinning positions 20.1, 20.2, 20.3, and 20.4 are thus connected jointly to the central machine control station 5 via the machine network 4 and to the analysis station 7 via the parallel analysis network 6. In addition to the control components 2.2 to 2.6 of the spinning position, the control component 2.1 of the extruder 11 is also designed having two network connections 8.1 and 8.2 in order to connect to the machine network 4 and the analysis network 6. Here, by way of example, a pressure sensor 36 on the extruder 11 is associated with control component 2.1. It is thus possible to take into consideration all machine components used in the machine system during the data analysis. With regard to so-called big-data analysis, the analysis station 7 has an Internet interface 9. Via the Internet interface 9, it is possible to connect the analysis station 7 to a diagnosis station 35. Here, the diagnosis station 35 may have both a local and a digital storage medium via which corresponding mass data can be processed. In this respect, comprehensive process analyses can be carried out on the basis of real-time parameters.

In order to be able to control fastest-possible process changes at the machine components, the analysis station 7 is connected to the machine control station 5 for data exchange.

FIGS. 3 and 4 depict several views of a further exemplary embodiment of a machine system for treating yarns. The exemplary embodiment relates to a texturing machine which is depicted in FIG. 3 in a cross-sectional view and in FIG. 4 in a top view. If no explicit reference is made to one of the figures, the following description applies to both figures.

The machine system provided for texturing yarns comprises a plurality of processing points per yarn, wherein hundreds of yarns are treated simultaneously inside the machine system. The processing stations are identically designed inside the machine system and have multiple machine components in each case for controlling the treatment process.

FIG. 3 depicts the machine components 1.1 to 1.8 of one of the processing stations. In this exemplary embodiment, the machine components 1.1 to 1.8 are formed by a first feed system 21, a heating apparatus 22, a texturing apparatus 25, a second feed system 26, a set heating apparatus 27, a third feed system 28, a spooling apparatus 29, and a changing apparatus 30.

The machine components 1.1 to 1.8 are arranged inside a machine frame 24 for a yarn path, in order to carry out a texturing process. For this purpose, the yarn 33 is kept ready by means of a supply bobbin 38 in a creel frame 37. The yarn 33 is extracted from the feed system 21 and, inside the texturing zone, is heated by the heating apparatus 22 and subsequently cooled in a cooling apparatus 23. Subsequently, the texturing apparatus 25 follows the second feed system 26, wherein the yarn 33 is drawn in the texturing zone. After post-treatment in the set heating apparatus 27, the yarn is guided from the third feed system 28 to the spooling apparatus 29 and wound onto a spool 34.

Since the spooling apparatus 29 requires a greater machine width in comparison to the upstream machine components 1.1 to 1.6, several spooling apparatuses 29 are arranged in a tiered manner in the machine frame 24. Separate control components 2.1 to 2.8 are associated in each case with the machine components 1.1 to 1.8 provided in the processing station, in order to control the respective machine components 1.1 to 1.8 with the associated actuators and sensors. The control components 2.1 to 2.8 respectively have two network connections 8.1 and 8.2. The network connection 8.2 is designed as a real-time network connection and is connected to an analysis network 6, for example, a ProfiNet. The parallel network connection 8.1 of the control components 2.1 to 2.8 is connected to the machine network 4. The machine network 4, which, for example, is formed by an Industrial Ethernet, connects the control components 2.1 to 2.8 to a section control station 31.1. The analysis network 6 connects the control components 2.1 to 2.8 in parallel to a section analysis station 32.

As is apparent from the depiction in FIG. 4, the machine components are combined from a total of twelve processing stations into a machine section 3.1. The control components 2.1 to 2.8 of the machine components 1.1 to 1.8 provided inside the machine section 3.1 are all integrated into the machine network 4 and are connected to the section control station 31.1. Accordingly, the control components 2.1 to 2.8 of the machine section 3.1 are connected to the section analysis station 32.1 via the analysis network 6.

A plurality of machine sections are provided in the machine system, wherein in this exemplary embodiment, only two of the machine sections are depicted. The section control stations 31.1 and 31.2 which are associated with the machine sections 3.1 and 3.2 are integrated into the machine network 4 and are coupled to a central machine control station 5. Accordingly, the section analysis stations 32.1 and 32.2 of the machine sections 3.1 and 3.2 are also integrated into the analysis network 6 and are connected to a central analysis station 7. The analysis station 7 is connected to an external diagnosis station 35 via an Internet interface 9.

The function for communication and data transfer takes place here analogously to the aforementioned exemplary embodiment, such that the real-time parameters and data can be directly supplied to the analysis station 7 via the analysis network 6. In this case, first pre-analyses can optionally be carried out via the section analysis station which is associated with the respective machine section. The analysis station 7 is connected to the machine control station 5 for direct data exchange. The entire machine system for texturing the yarns can be controlled via the central machine control station 5. The monitoring and analysis preferably take place via the central analysis station 7. In the case of a large quantity of data, it is possible to integrate the external diagnosis station 35 into the analysis and the diagnosis.

The machine system according to the present invention for producing and/or treating synthetic yarns is characterized in particular by a quality analysis based on real-time data. It is thus possible to carry out process optimizations during the ongoing production process or treatment process. In the case of process disturbances, corresponding diagnoses can be carried out via the real-time parameter transmission, independently of the machine control. In addition, it is possible to ascertain anticipatory maintenance from the data analysis.

In order to minimize the wiring effort inside the machine system for implementing the machine network and the analysis network, there is also the possibility of implementing at least one of the networks wirelessly. Thus, the machine network could, for example, be configured as a radio network. Preferably, it is possible to implement the wireless network according to a WLAN standard, so that all control components are connected to the central machine control station via a local machine radio network. Analogously, however, a real time-capable analysis radio network could be installed in the machine system.

The invention claimed is:

1. A machine system for producing or treating synthetic yarns, the machine system comprising:
   a plurality of machine components constructed and arranged to perform a process of producing synthetic yarns, the machine components having actuators and/or sensors to influence the process of producing synthetic yarns;
   a plurality of control components associated with the plurality of machine components, each control component of the plurality of control components having:
      a first network connection which connects with a machine network,
      a second network connection which connects with an analysis network, and
      a third connection which connects with a respective machine component of the plurality of machine components;
   a central machine control station programmed to control the machine components via the first network connections of the control components and the machine network;
   a central analysis station programmed to perform real time monitoring and analysis of the process of producing synthetic yarns via the second network connections of the control components and the analysis network;
   wherein the control components communicate with the central machine control station through the first network connections and the machine network;
   wherein the control components communicate with the central analysis station through the second network connections and the analysis network;
   wherein the control components communicate with the machine components through the third connections; and
   wherein isolation between the machine network and the analysis network enables the central machine control station and the central analysis station to communicate with the control components in parallel.

2. The machine system as claimed in claim 1, wherein the analysis network is formed by means of a real time-capable bus system for data transmission.

3. The machine system as claimed in claim 1, wherein the machine network is formed by means of an Industrial Ethernet for data transmission.

4. The machine system as claimed claim 1, wherein the control components have at least two network connections, wherein one of the network connections is configured as a real-time network connection.

5. The machine system as claimed in claim 1, wherein the machine control station is connected to the analysis network via a separate real-time network connection.

6. The machine system as claimed in claim 1, wherein the central analysis station has an Internet interface, and the central analysis station is connected to an external diagnosis station.

7. The machine system as claimed in claim 1, wherein the central analysis station and the central machine control station are interconnected for data exchange.

8. The machine system as claimed in claim 1, wherein the machine network and/or the analysis network is configured wirelessly according a wireless local area network (WLAN) standard.

\* \* \* \* \*